United States Patent
Stauss

(10) Patent No.: US 11,512,978 B2
(45) Date of Patent: Nov. 29, 2022

(54) SCANNER FOR DIFFERENTIATING OBJECTS DETECTED BEHIND AN OPAQUE SURFACE

(71) Applicant: Zircon Corporation, Campbell, CA (US)

(72) Inventor: John Robert Stauss, Los Gatos, CA (US)

(73) Assignee: Zircon Corporation, Campbell, CA (US)

(*) Notice: Subject to any disclaimer, the term of this patent is extended or adjusted under 35 U.S.C. 154(b) by 417 days.

(21) Appl. No.: 16/698,751

(22) Filed: Nov. 27, 2019

(65) Prior Publication Data

US 2021/0156715 A1 May 27, 2021

(51) Int. Cl.
| | | |
|---|---|---|
| G01R 27/26 | (2006.01) | |
| G01D 5/06 | (2006.01) | |
| G01N 27/72 | (2006.01) | |
| G01D 5/24 | (2006.01) | |

(52) U.S. Cl.
CPC ............. *G01D 5/06* (2013.01); *G01D 5/24* (2013.01); *G01N 27/72* (2013.01)

(58) Field of Classification Search
USPC ................. 324/660–663, 679, 686, 71.1
See application file for complete search history.

(56) References Cited

U.S. PATENT DOCUMENTS

| | | | |
|---|---|---|---|
| 5,619,128 A | 4/1997 | Heger | |
| 6,215,293 B1 | 4/2001 | Yim | |
| 6,933,712 B2 | 4/2005 | Miller et al. | |
| 6,894,508 B2 | 5/2005 | Sanoner et al. | |
| 7,504,817 B2 | 3/2009 | Sanoner et al. | |
| 7,583,071 B2 | 9/2009 | Skultety-Betz et al. | |
| 7,671,577 B2 | 3/2010 | Skultety-Betz et al. | |
| 7,701,191 B2 | 4/2010 | Skultety-Betz et al. | |
| 7,764,061 B2 | 7/2010 | Skultety-Betz et al. | |
| 7,812,722 B2 | 10/2010 | Krantz | |
| 7,977,938 B2 | 7/2011 | Sanoner et al. | |
| 8,274,273 B2 | 9/2012 | Nguyen et al. | |
| 8,546,759 B2 | 10/2013 | Skultety-Betz et al. | |
| 9,959,591 B2 * | 5/2018 | Sendai ............... | G02B 27/0172 |

(Continued)

OTHER PUBLICATIONS

International Search Report and Written Opinion dated Feb. 1, 2021, from PCT Application No. PCT/US2020/58677, filed Nov. 3, 2020.

*Primary Examiner* — Vincent Q Nguyen
(74) *Attorney, Agent, or Firm* — Silicon Valley Patent Group LLP; Thomas C. Chan

(57) ABSTRACT

Aspects of the present invention include a system and method for differentiating a plurality of objects detected behind an opaque surface, including, a plurality of sensors, controlled by one or more processors, configured to collect in parallel, sensor data of the plurality of objects behind an opaque surface, the one or more processors are configured to analyze the sensor data to identify estimated regions of the plurality of objects behind the opaque surface, the one or more processors are further configured to differentiate the estimated regions of the plurality of objects behind the opaque surface, and, the one or more processors are further configured to inform a user, via a user interface, of the plurality of objects within the estimated regions behind the opaque surface.

18 Claims, 10 Drawing Sheets

(56) References Cited

U.S. PATENT DOCUMENTS

| | | |
|---|---|---|
| 2003/0218469 A1 | 11/2003 | Brazell et al. |
| 2007/0210785 A1* | 9/2007 | Sanoner ............... G01R 29/085 |
| | | 324/67 |
| 2011/0311328 A1 | 12/2011 | Barr et al. |
| 2014/0043046 A1 | 2/2014 | Adams et al. |
| 2014/0145704 A1 | 5/2014 | Krapf et al. |
| 2016/0077232 A1* | 3/2016 | Wingate ................... G01V 3/15 |
| | | 324/67 |
| 2016/0103215 A1 | 4/2016 | Watts et al. |
| 2019/0021631 A1* | 1/2019 | Cohen ................... A61B 90/39 |
| 2019/0063679 A1 | 2/2019 | Mergener |
| 2019/0219721 A1* | 7/2019 | Dorrough .............. G01V 3/081 |

* cited by examiner

SCANNER FOR DIFFERENTIATING OBJECTS DETECTED BEHIND AN OPAQUE SURFACE

FIELD

The present invention relates to the field of scanners for differentiating one or more objects detected behind an opaque surface.

BACKGROUND

As an example, stud finders have been commonly used in construction and home improvement industries. FIG. 1 illustrates a side view of a conventional scanner. As shown in FIG. 1, a scanner 102 may be used in a construction and home improvement environment 100. For example, scanner 102 may be configured to detect an object 101 behind an opaque surface 103. In some exemplary applications, object 101 may be a stud, an electrical wire, or a metal pipe. In one exemplary embodiment, the stud may be a wooden stud, vertical wooden element, bridging block, fire block, or any other block, joists, rafters, headers, posts, columns, let brace, or any similar wooden element used for integrity, fabrication, or maintenance of a structural element. In one exemplary embodiment, opaque surface 103 may be, for example, a wall covered with drywall, particle board, or plywood; as an example, a floor with opaque material attached to structural members; as an example, a ceiling with an opaque surface, attached to rafters; or any other opaque surface behind which objects are not visible through the surface.

In one exemplary embodiment, scanner 102 may include a housing to enclose and protect various electronic components. For example, within the housing of the scanner 102, it may include a printed circuit board (PCB) 104, which can be configured to hold the various electronic components, such as one or more capacitive sensor(s) 108, one or more metal sensors 109, one or more current sensors (not shown), a controller/processor and other integrated circuits (labelled as 106a and 106b). The PCB 104 may be coupled to a battery 107, which provides power to the scanner 102. In conventional applications, the one or more capacitive sensor(s) 108, one or more metal sensors 109, and one or more current sensors are typically operated individually or separately. However, such conventional applications may be insufficient to address the complexity of differentiating one or more objects behind the opaque surface 103.

Therefore, there is a need for a scanner that can address the above drawbacks of the conventional scanner in differentiating one or more objects detected behind an opaque surface.

SUMMARY

Aspects of the present disclosure include an exemplary system for differentiating one or more objects detected behind an opaque surface, comprising, a plurality of sensors, controlled by one or more processors, configured to collect in parallel, sensor data of the one or more objects behind an opaque surface, the one or more processors are configured to analyze the sensor data to identify estimated regions of the one or more objects behind the opaque surface, the one or more processors are further configured to differentiate the estimated regions of the one or more objects behind the opaque surface, and, the one or more processors are further configured to inform a user, via a user interface, of the one or more objects within the estimated regions behind the opaque surface.

Aspects of the present invention include a method for differentiating one or more objects detected behind an opaque surface, comprising, collecting in parallel sensor data of the one or more objects behind an opaque surface by a plurality of sensors controlled by one or more processors, analyzing by the one or more processors the sensor data to identify estimated regions of the one or more objects behind the opaque surface, differentiating by the one or more processors the estimated regions of the one or more objects behind the opaque surface, and informing a user, by the one or more processors, of the one or more objects within the estimated regions behind the opaque surface.

BRIEF DESCRIPTION OF THE DRAWINGS

The aforementioned features and advantages of the invention, as well as additional features and advantages thereof, will be more clearly understandable after reading detailed descriptions of embodiments of the invention in conjunction with the non-limiting and non-exhaustive aspects of the following drawings. Like numbers are used throughout the disclosure.

DESCRIPTION OF EMBODIMENTS

Methods and apparatuses are provided for differentiating one or more objects detected behind an opaque surface. The following descriptions are presented to enable a person skilled in the art to make and use the invention. Descriptions of specific embodiments and applications are provided only as examples. Various modifications and combinations of the examples described herein may be readily apparent to those skilled in the art, and the general principles defined herein may be applied to other examples and applications without departing from the scope of the invention. Thus, the present invention is not intended to be limited to the examples described and shown, but is to be accorded the scope consistent with the principles and features disclosed herein. The word "exemplary" or "example" is used herein to mean "serving as an example, instance, or illustration." Any aspect or embodiment described herein as "exemplary" or as an "example" is not necessarily to be construed as preferred or advantageous over other aspects or embodiments.

Some portions of the detailed description that follow are presented in terms of flowcharts, logic blocks, and other symbolic representations of operations on information that can be performed on a computer system. A procedure, computer-executed step, logic block, process, etc., is here conceived to be a self-consistent sequence of one or more steps or instructions leading to a desired result. The steps are those utilizing physical manipulations of physical quantities. These quantities can take the form of electrical, magnetic, or radio signals capable of being stored, transferred, combined, compared, and otherwise manipulated in a computer system. These signals may be referred to at times as bits, values, elements, symbols, characters, terms, numbers, or the like. Each step may be performed by hardware, software, firmware, or combinations thereof.

The drawings are presented for illustration purposes, and they are not drawn to scale. In some examples, rectangles, circles or other shapes are used to illustrate shapes of objects and their respective estimated shapes of the objects. In real world applications, the shapes of objects and their respective estimated shapes of the objects may be irregular and may be in any shapes or forms. Note that in the following figures, for each object, a section of the object, not the entire object, is shown. This also applies to the respective estimated shape of each object.

Figure 1:
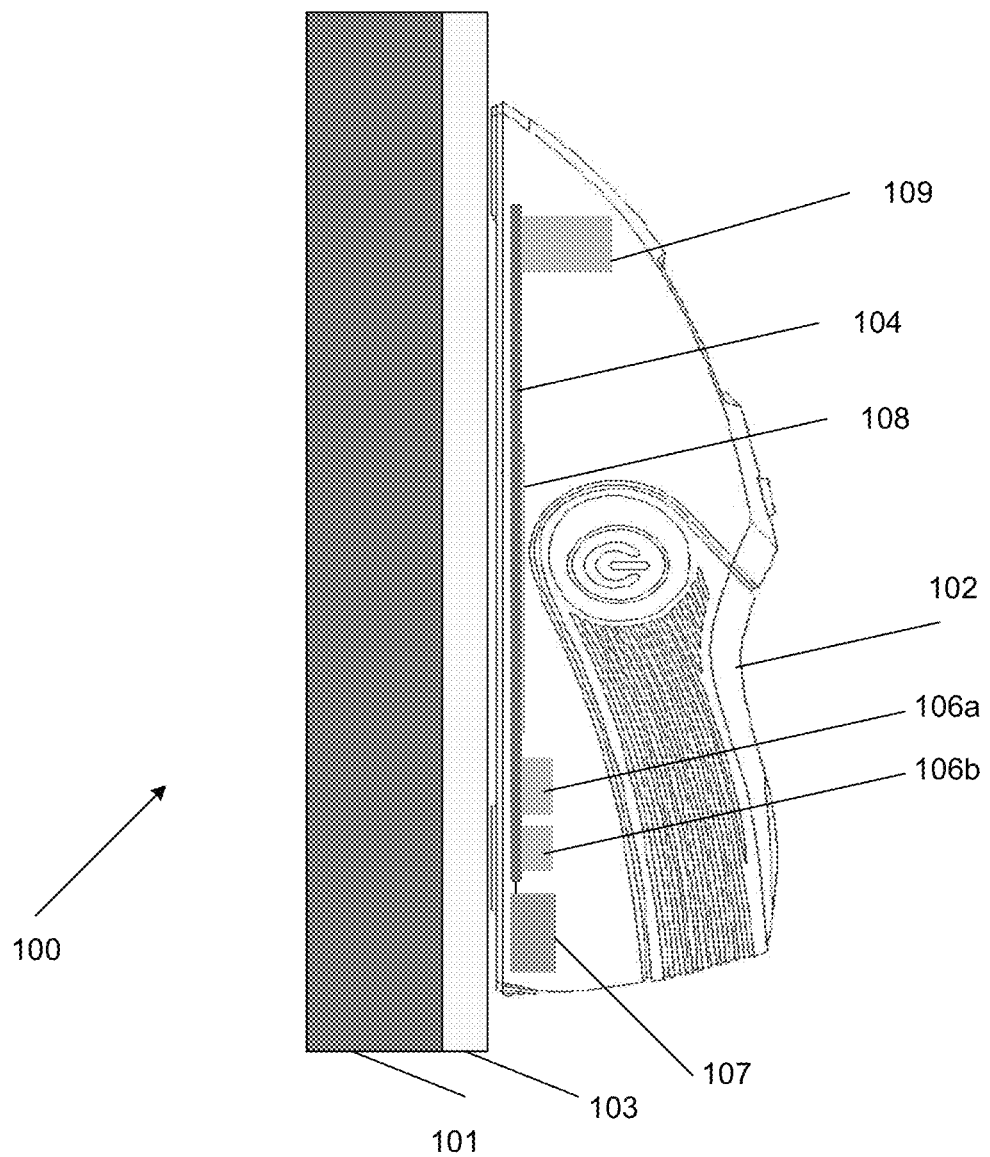
FIG. 1 illustrates a side view of a conventional scanner.
Figure 2A:
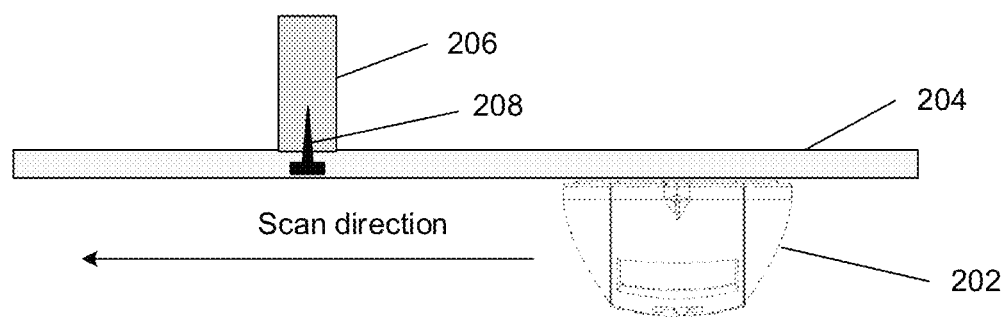
FIG. 2A illustrates a top view of an exemplary embodiment for differentiating one or more objects detected behind an opaque surface according to aspects of the present invention.

FIG. 2A illustrates a top view of an exemplary embodiment for differentiating one or more objects detected behind an opaque surface according to aspects of the present invention. As shown in FIG. 2A, the exemplary embodiment may include a scanner 202 an opaque surface 204, and one or more objects (labelled as 206, 208) behind the opaque surface 204. The scanner 202 may be configured to differentiate a variety of objects detected behind the opaque surface, including but not limited to, for example: 1) wood studs, wood joists, wood rafters; 2) metallic objects; 3) electrical wires; or 4) other objects. In the example of FIG. 2A, object 206 may be a wood stud, object 208 may be a metal pipe, and object 220 may be a current source.

Figure 2B:
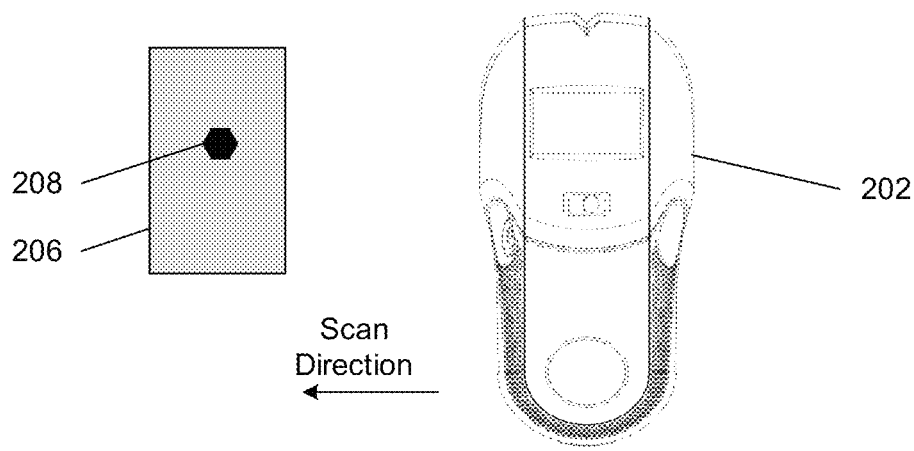
FIG. 2B illustrates a front view of the exemplary embodiment of FIG. 2A for differentiating one or more objects detected behind an opaque surface according to aspects of the present invention.

FIG. 2B illustrates a front view of the exemplary embodiment of FIG. 2A for detecting different objects behind an opaque surface according to aspects of the present invention. In the example of FIG. 2B, the opaque surface is not shown for simplicity. As shown in FIG. 2A and FIG. 2B, the scan direction may be from right to left. A person skilled in the art would understand that the scan direction may be adjusted based on the working environment, the preference of the user, and the specific application. In other words, the scan direction may be from left to right, right to left, up to down, down to up, or diagonally. In some applications, a user may perform multiple scans and/or from multiple directions to improve the accuracy of sensor data collected.

Figure 2C:
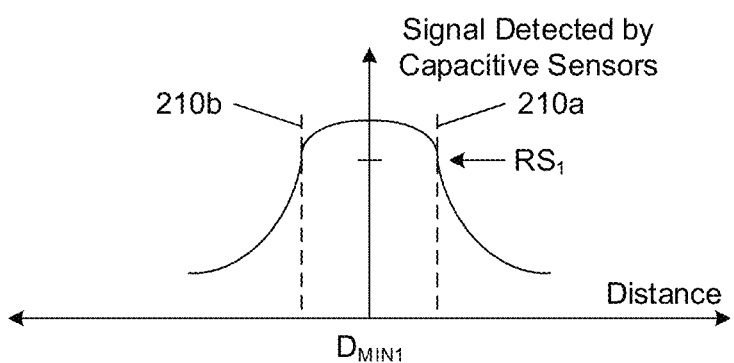
FIG. 2C illustrates a first set of sensor data collected by the scanner of FIG. 2B according to aspects of the present invention.

FIG. 2C illustrates a first set of sensor data collected by the scanner of FIG. 2B according to aspects of the present invention. In this example, the sensor data may be collected by one or more capacitive sensors of the scanner 202; and one or more items may be included in a set. The signal may represent a change of capacitance due to the change in the density of the objects behind the opaque surface, which may include an indication of the density of object 206 and object 208. The vertical axis represents a magnitude of the signal observed by the capacitive sensors, and the horizontal axis represents a distance of the capacitive sensors from the objects being detected. As the scanner 202 scans from right to left (as shown in FIG. 2B), the magnitude of the signal being observed by the capacitive sensors increases, reaching a plateau when the scanner is approximately above the center of the objects. As the scanner 202 continues to move pass the center of the objects, the magnitude of the signal being observed by the capacitive sensors decreases.

According to aspects of the present invention, a first reference signal strength ($RS_1$) may be used to identify the boundaries of object 206. For example, the region between the two dashed lines 210a and 210b has a signal strength at or above $RS_1$, and this region may be estimated to be where object 206 is located. On the other hand, the region outside of the two dashed lines 210a and 210b has a signal strength below $RS_1$, and this region may be estimated to be where object 206 is not found. When the signal magnitude detected by the capacitive sensors reaches the first reference signal strength $RS_1$, object 206 behind the opaque surface may be detected and the boundaries of object 206 may be recorded, as indicated by the dashed lines 210a and 210b in FIG. 2C.

Note that the first reference signal strength $RS_1$ may be derived from empirical experimental data. The first reference signal strength $RS_1$ may be programmable, and may be revised via a software update even after the scanner has been sold, the delivery methods of which are well known to those skilled in the art. At the center of the graph, the distance $D_{MIN1}$ represent a minimum distance between the capacitive sensors of the scanner 202 and the approximate center of the objects. Note that although a right to left scan is described in this example, similar observations may be obtained by a scan from left to right. In some applications, multiple scans from different directions may be used to improve the accuracy of the estimated boundaries of object 206.

Figure 2D:
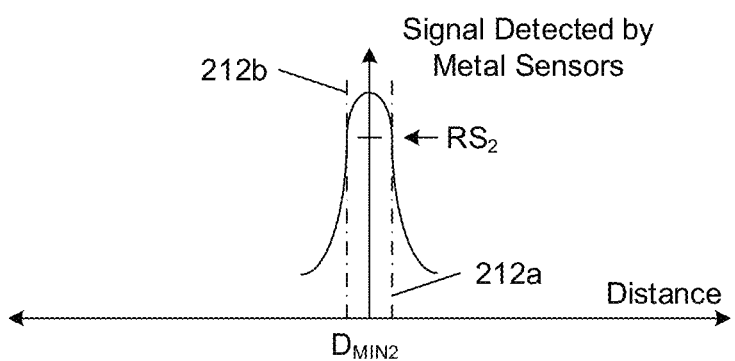
FIG. 2D illustrates a second set of sensor data collected by the scanner of FIG. 2B according to aspects of the present invention.

FIG. 2D illustrates a second set of sensor data collected by the scanner of FIG. 2B according to aspects of the present invention. In the example of FIG. 2D, the sensor data may be collected by one or more metal sensors of scanner 202; and one or more items may be included in a set. The signal may represent a magnetic field detected behind the opaque surface, primarily affected by the existence of a metal object, such as object 208. The vertical axis represents a magnitude of the signal observed by the metal sensors, and the horizontal axis represents a distance of the metal sensors from object 208. As scanner 202 scans from right to left (as shown in FIG. 2B), the magnitude of the signal being observed by the metal sensors increases, reaching a plateau when the scanner is approximately above the center of object 208. As scanner 202 continues to move past the center of object 208, the magnitude of the signal being observed by the metal sensors decreases.

According to aspects of the present invention, a second reference signal strength ($RS_2$) may be used to identify the boundaries of object 208. For example, the region between the two dashed lines 212a and 212b has a signal strength at or above $RS_2$, and this region may be estimated to be where object 208 is located. On the other hand, the region outside of the two dashed lines 212a and 212b has a signal strength below $RS_2$, and this region may be estimated to be where object 208 is not found. When the signal magnitude detected by the metal sensors reaches the second reference signal strength $RS_2$, object 208 behind the opaque surface may be detected, and the boundaries of object 208 may be recorded, as indicated by the dashed lines 212a and 212b in FIG. 2D.

Note that the second reference signal strength $RS_2$ may be derived from empirical experimental data. The second reference signal strength $RS_2$ may be programmable, and may be revised via a software update even after the scanner 202 has been sold, the delivery methods of which are well known to those skilled in the art. At the center of the graph, the distance $D_{MIN2}$ represents a minimum distance between the metal sensors of scanner 202 and the approximate center of object 208. Note that although a right to left scan is described in this example, similar observations may be obtained by a scan from left to right. In some applications, multiple scans from different directions may be used to improve the accuracy of the estimated boundaries of object 208.

Figure 3A:
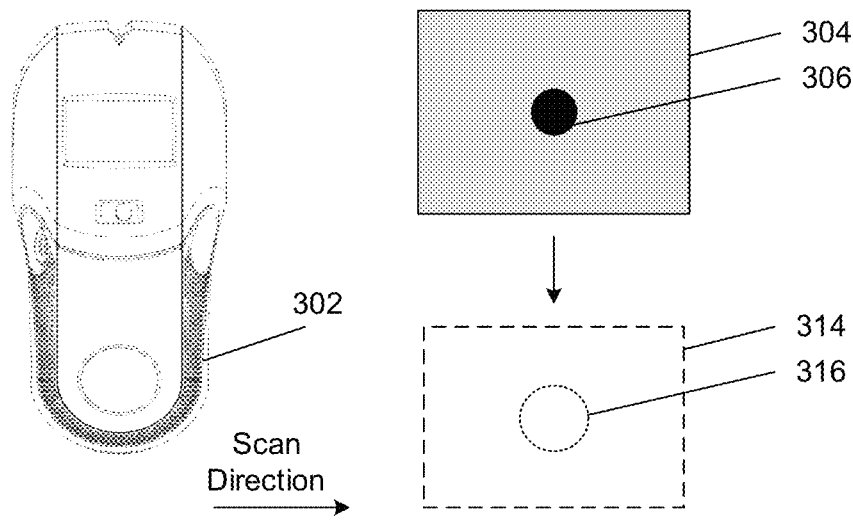
FIG. 3A illustrates a front view of another exemplary embodiment for differentiating one or more objects detected behind an opaque surface according to aspects of the present invention.

FIG. 3A illustrates a front view of another exemplary embodiment for detecting different objects behind an opaque surface according to aspects of the present invention. As shown in FIG. 3A, the exemplary embodiment may include a scanner 302 and one or more objects (labelled as 304 and 306) behind an opaque surface. Note that, for simplicity, the opaque surface is not shown. Object 304 may be a wood stud, and object 306 may be a metal pipe. The scan direction may be from left to right. The method described above in association with FIG. 2A to FIG. 2D may be employed to determine an estimated region for each object behind the opaque surface, which is not repeated here. In this example, rectangle 314 represents an estimated region of object 304, and circle 316 represents an estimated region of object 306.

Figure 3B:
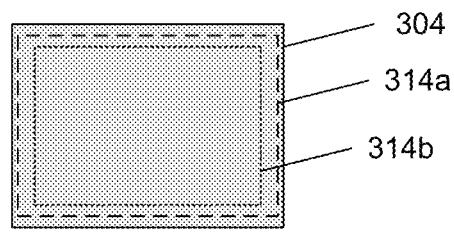
FIG. 3B illustrates an exemplary embodiment of determining an estimated region of an object of FIG. 3A according to aspects of the present invention.

FIG. 3B illustrates an exemplary method of determining an estimated region of an object of FIG. 3A according to aspects of the present invention. As shown in FIG. 3B, the method of determining the estimated region of object 304 is used as an example. Compared to the actual object 304, a first estimated region 314a can be determined by employing the first reference signal strength ($RS_1$) as described in association with FIG. 2C. Since the first reference signal strength may be programmable, for a wood stud, it can be programmed to provide the first estimated region 314a to be smaller than the actual object 304. By choosing the first estimated region 314a to be smaller than the actual object 304, this approach can provide the benefit of having a higher level of confidence that a wood stud is hit when a user drills into the opaque surface.

Additionally or optionally, a second estimated region 314b can be determined by inserting a safety margin. This safety margin is represented by the area between the first estimated region 314a and the second estimated region 314b. Various factors may be used to determine the safety margin, including but not limited to: 1) type of material of the opaque surface; 2) humidity of the environment; 3) temperature of the environment; or 4) other factors that may affect the accuracy of determining the estimated region of object 304. The safety margin may add 2 mm, 4 mm, or other measurements on each side of the first estimated region to form the second estimated region based on the above factors and the design criteria for the scanner. Depending on the application, either the first estimated region 314a or the second estimated region 314b may be used to represent the estimated region of object 304.

Figure 3C:
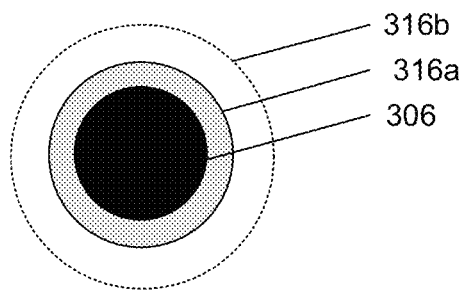
FIG. 3C illustrates another exemplary embodiment of determining an estimated region of another object of FIG. 3A according to aspects of the present invention.

FIG. 3C illustrates another exemplary method of determining an estimated region of another object of FIG. 3A according to aspects of the present invention. As shown in FIG. 3C, the method of determining the estimated region of object 306 is used as an example. Compared to the actual object 306, a first estimated region 316a can be determined by employing the second reference signal strength ($RS_2$) as described in association with FIG. 2D. Since the second reference signal strength may be programmable, for a metal pipe, it can be programmed to provide the first estimated region 316a to be larger than the actual object 306, for example larger by 1 millimeter (mm), 3 mm, or other measurements on each side of the first estimated region based on design criteria for the scanner. By choosing the first estimated region 316a to be larger than the actual object 306, this approach can provide the benefit of having a higher level of confidence that a metal object is missed when the user drills into the opaque surface.

Additionally or optionally, a second estimated region 316b can be determined by inserting a safety margin. This safety margin is represented by the area between the first estimated region 316a and the second estimated region 316b. Various factors may be used to determine the safety margin, including but not limited to: 1) type of material of the opaque surface; 2) humidity of the environment; 3) temperature of the environment; or 4) other factors that may affect the accuracy of determining the estimated region of object 306. Depending on the application, either the first estimated region 316a or the second estimated region 316b may be used to represent the estimated region of object 306.

Figure 3D:
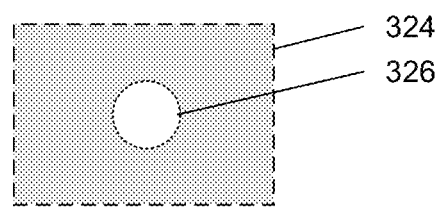
FIG. 3D illustrates an exemplary embodiment of displaying the estimated regions of the different objects of FIG. 3A according to aspects of the present invention.

FIG. 3D illustrates an exemplary implementation of displaying the estimated regions of the different objects of FIG. 3A according to aspects of the present invention. According to aspects of the present disclosure, a user interface can mean any form of communication to a user, including, but not limited to, visual (for example via a display or one or more light emitting diodes), audible (for example via a speaker) or sensory (for example via a vibration). The information being communicated may be displayed, streamed, stored, mapped, or distributed across multiple devices. Communication to the user can mean either the user or any other person or object which can receive communication. In one approach, when multiple objects are detected, the method determines regions where a single object is detected as well as regions where multiple objects are detected. In the example shown in FIG. 3D, metal pipe 326 may represent a region where multiple objects are detected (for example, which region includes part of stud 324), and rectangle 324 (which includes part of metal pipe 326) may represent a region where a part of it has multiple objects (for example, part of metal pipe 326 and part of stud 324) and another part of it (excluding the remainder of metal pipe 326 and the region that includes both stud 324 and metal pipe 326) has a single object.

Based on the above information, for the region of metal pipe 326, the display may be configured to display the multiple objects detected behind the opaque surface for this region. For the region of stud 324 that excludes metal pipe 326, the display may be configured to display the single object detected behind the opaque surface. In some implementations, for the region of metal pipe 326, depending on the types of objects detected, such as wood stud and metal pipe in this example, the display may be configured to display nothing for the region of metal pipe 326.

Figure 4A:
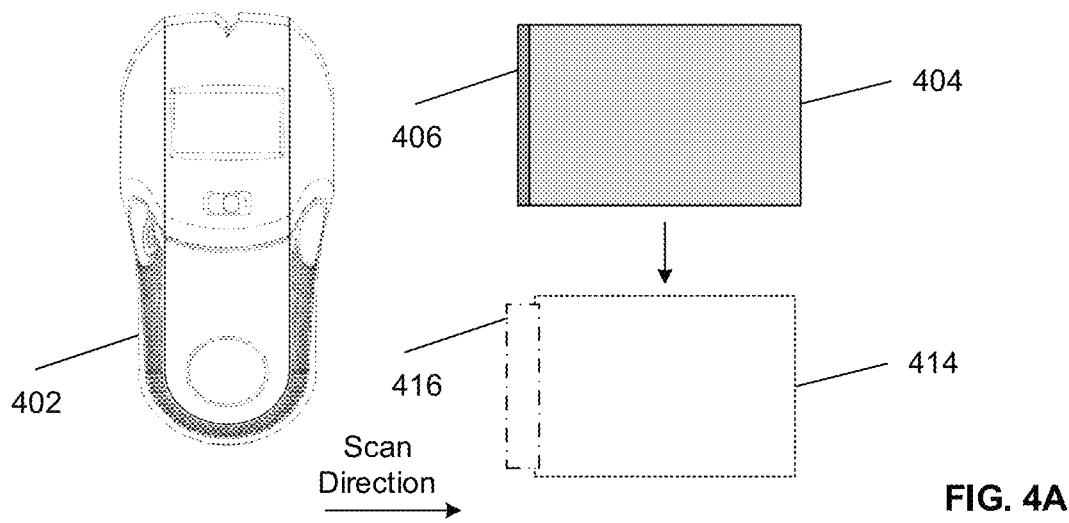
FIG. 4A illustrates a front view of yet another exemplary embodiment for differentiating one or more objects detected behind an opaque surface according to aspects of the present invention.

FIG. 4A illustrates a front view of yet another exemplary embodiment for differentiating one or more objects detected behind an opaque surface according to aspects of the present invention. As shown in FIG. 4A, the exemplary embodiment may include a scanner 402, and one or more objects (labelled as 404 and 406) behind an opaque surface. Note that the opaque surface is not shown for simplicity. Object 404 may be a wood stud, and object 406 may be an electrical wire. The scan direction may be from left to right. The method described above in association with FIG. 2A to FIG. 2D may be employed to determine an estimated region for each object behind the opaque surface, which is not repeated here. In this example, rectangle 414 represents an estimated region of object 404, and rectangle 416 represents an estimated region of object 406.

Figure 4B:
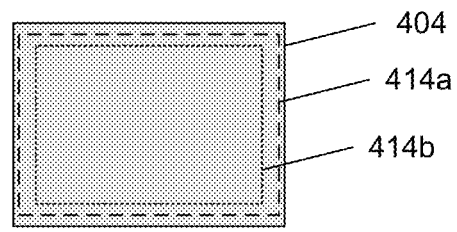
FIG. 4B illustrates an exemplary embodiment of determining an estimated region of an object of FIG. 4A according to aspects of the present invention.

FIG. 4B illustrates an exemplary method of determining an estimated region of an object of FIG. 4A according to aspects of the present invention. As shown in FIG. 4B, the method of determining the estimated region of object 404 is used as an example. Compared to the actual object 404, a first estimated region 414a can be determined by employing the first reference signal strength ($RS_1$) as described in association with FIG. 2C. Since the first reference signal strength may be programmable, for a wood stud, for example, it can be programmed to provide the first estimated region 414a to be smaller than the actual object 404, for example smaller by 2 mm, 4 mm, or other measurements on each side of the first estimated region based on design criteria for the scanner. By choosing the first estimated region 414a to be smaller than the actual object 404, this approach can provide the benefit of having a higher level of confidence that a wood stud is hit when a user drills into the opaque surface.

Additionally or optionally, a second estimated region 414b can be determined by inserting a safety margin. This safety margin is represented by the area between the first estimated region 414a and the second estimated region 414b. Various factors may be used to determine the safety margin, including but not limited to: 1) type of material of the opaque surface; 2) humidity of the environment; 3) temperature of the environment; or 4) other factors that may affect the accuracy of determining the estimated region of object 404. Depending on the application, either the first estimated region 414a or the second estimated region 414b may be used to represent the estimated region of object 404.

Figure 4C:
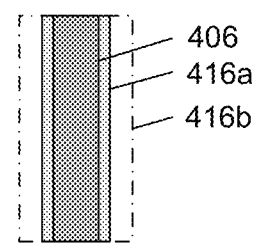
FIG. 4C illustrates another exemplary embodiment of determining an estimated region of another object of FIG. 4A according to aspects of the present invention.

FIG. 4C illustrates another exemplary method of determining an estimated region of another object of FIG. 4A according to aspects of the present invention. As shown in FIG. 4C, the method of determining the estimated region of object 406 is used as an example. Compared to the actual object 406, a first estimated region 416a can be determined by employing a third reference signal strength ($RS_3$) similar to the description in association with FIG. 2D. The third reference signal strength may be programmable. For example, for an electrical wire, it can be programmed to provide the first estimated region 416a to be larger than the actual object 406, for example larger by 3 mm, 5 mm, or other measurements on each side of the first estimated region based on design criteria for the scanner. By choosing the first estimated region 416a to be larger than the actual object 406, this approach can provide the benefit of having a higher level of confidence that an electrical wire is missed when a user drills into the opaque surface.

Additionally or optionally, a second estimated region 416b can be determined by inserting a safety margin. This safety margin is represented by the area between the first estimated region 416a and the second estimated region 416b. Various factors may be used to determine the safety margin, including but not limited to: 1) type of material of the opaque surface; 2) humidity of the environment; 3) temperature of the environment; or 4) other factors that may affect the accuracy of determining the estimated region of object 406. The safety margin may add 1 mm, 3 mm, or other measurements on each side of the first estimated region to form the second estimated region based on the above factors and the design criteria for the scanner. Depending on the application, either the first estimated region 416a or the second estimated region 416b may be used to represent the estimated region of object 406.

Figure 4D:
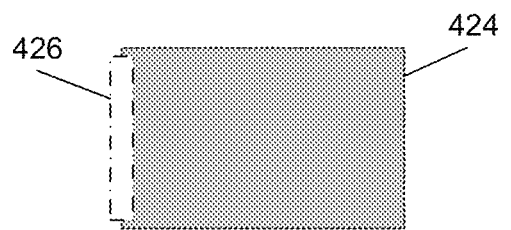
FIG. 4D illustrates an exemplary embodiment of displaying the estimated regions of the different objects of FIG. 4A according to aspects of the present invention.

FIG. 4D illustrates an exemplary implementation of displaying the estimated regions of the different objects of FIG. 4A according to aspects of the present invention. In one approach, when multiple objects are detected, the method determines regions where a single object is detected as well as regions where multiple objects are detected. In the example shown in FIG. 4D, rectangle 426 may represent a region where multiple objects are detected, and rectangle 424 (which includes part of rectangle 426) may represent a region where a part of it has multiple objects (for example the region that overlaps with rectangle 426) and another part of it (excluding the region that overlaps with rectangle 426) has a single object.

Based on the above information, for the region of the rectangle 426, the display may be configured to display the multiple objects detected behind the opaque surface for this region. For the region of the rectangle 424 that excludes the rectangle 426, the display may be configured to display the single object detected behind the opaque surface. In some implementations, for the region of the rectangle 426, depending on the types of objects detected, such as wood stud and electrical wire in this example, the display may be configured to display nothing for the region of the rectangle 426.

Figure 5A:
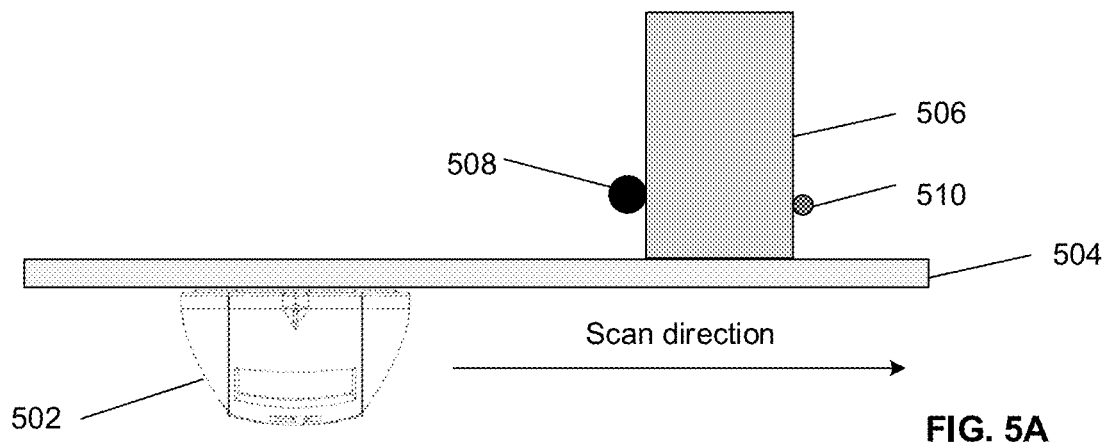
FIG. 5A illustrates a top view of yet another exemplary embodiment for differentiating one or more objects detected behind an opaque surface according to aspects of the present invention.

FIG. 5A illustrates a top view of yet another exemplary embodiment for differentiating one or more objects detected behind an opaque surface according to aspects of the present invention. As shown in FIG. 5A, the exemplary embodiment may include a scanner 502, an opaque surface 504, and one or more objects (labelled as 506, 508, and 510) behind the opaque surface 504. The scanner 502 may be configured to detect a variety of objects behind the opaque surface, including but not limited to: 1) wood studs; 2) metallic objects; 3) electrical wires; or 4) other objects. In the example of FIG. 5A, object 506 may be a wood stud, and object 508 may be a metal pipe, and object 510 may be an electrical wire.

Figure 5B:
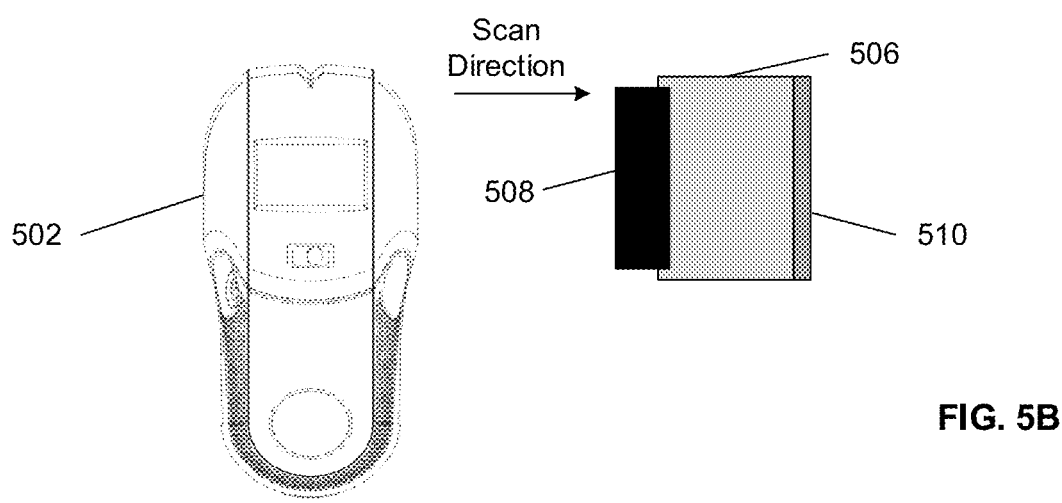
FIG. 5B illustrates a front view of the exemplary embodiment of FIG. 5A for differentiating one or more objects detected behind an opaque surface according to aspects of the present invention.

FIG. 5B illustrates a front view of the exemplary embodiment of FIG. 5A for detecting object(s) behind an opaque surface according to aspects of the present invention. In the example of FIG. 5B, the opaque surface is not shown for simplicity. As shown in FIG. 5A and FIG. 5B, the scan direction may be from right to left. A person skilled in the art would understand that the scan direction may be adjusted based on the working environment, the preference of the user, and the specific application. In other words, the scan direction may be from left to right, right to left, up to down, down to up, or diagonally. In some applications, a user may perform multiple scans and/or from multiple directions to improve the accuracy of sensor data collected.

Figure 5C:
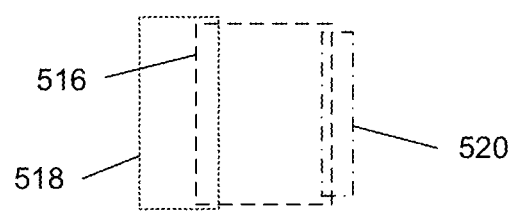
FIG. 5C illustrates estimated exemplary regions of the different objects of FIG. 5B according to aspects of the present invention.

FIG. 5C illustrates estimated regions of the different objects of FIG. 5B according to aspects of the present invention. Note that the method of determining an estimated region of an object is described above, for example in association with FIG. 3B and FIG. 3C, which is not repeated here. As shown in FIG. 5C, rectangle 516 represents an estimated region for stud 506, rectangle 518 represents an estimated region for metal pipe 508, and rectangle 520 represents an estimated region for electrical wire 510.

In this particular example, since the object 506 is a wood stud, the estimated region 516 can be configured to be smaller than stud 506, this approach can provide the benefit of having a higher level of confidence that a wood stud 506 is penetrated by a drill bit when a user drills through the opaque surface. Since the object 508 is a metal pipe, the estimated region 518 can be configured to be larger than metal pipe 508, this approach can provide the benefit of having a higher level of confidence that metal pipe 508 is missed when a user drills through the opaque surface. Similarly, since the object 510 is an electrical wire, the estimated region 520 can be configured to be larger than electrical wire 510, this approach can provide the benefit of having a higher level of confidence that electrical wire 510 is missed when a user drills through the opaque surface.

Figure 5D:
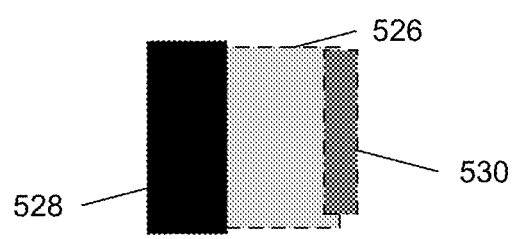
FIG. 5D illustrates an exemplary embodiment of displaying the estimated regions of the different objects of FIG. 5C according to aspects of the present invention.

FIG. 5D illustrates an exemplary implementation of displaying the estimated regions of the different objects of FIG. 5C according to aspects of the present invention. With the estimated region 516 being configured to be smaller than stud 506 while the estimated region 518 being configured to be larger than metal pipe 508, and the estimated region 520 being configured to be larger than electrical wire 510. In some implementations, the display may be configured to display the estimated region for stud 506, represented by rectangle 526, and display the estimated region for metal pipe 508, represented by rectangle 528, and display the estimated region for electrical wire 510, represented by the rectangle 530. In some other implementations, the display may be configured to display the region under the rectangle 528 to include both metal pipe 508 and wood stud 506, and display the region under the rectangle 530 to include both electrical wire 510 and wood stud 506.

Figure 6A:
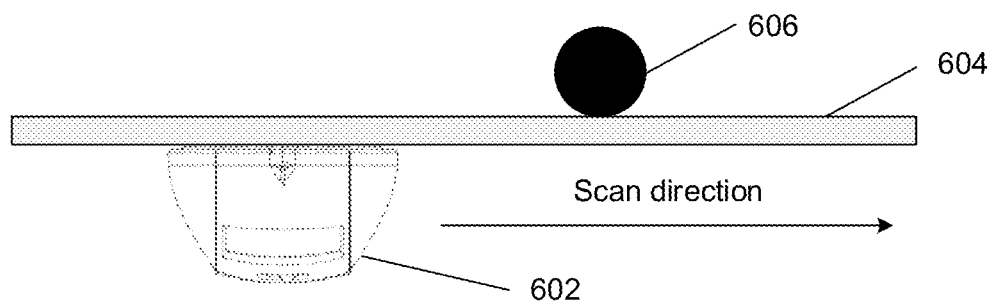
FIG. 6A illustrates a top view of an exemplary embodiment for differentiating one or more objects detected behind an opaque surface using sensor data from different sensors according to aspects of the present invention.

FIG. 6A illustrates a top view of an exemplary embodiments for differentiating one or more objects detected behind an opaque surface using sensor data from different sensors according to aspects of the present invention. In the example shown in FIG. 6A, the exemplary embodiment may include a scanner 602, an opaque surface 604, and one or more objects (labelled as 606) behind the opaque surface 604. In the example of FIG. 6A, object 606 may be, for example, a metal pipe.

Figure 6B:
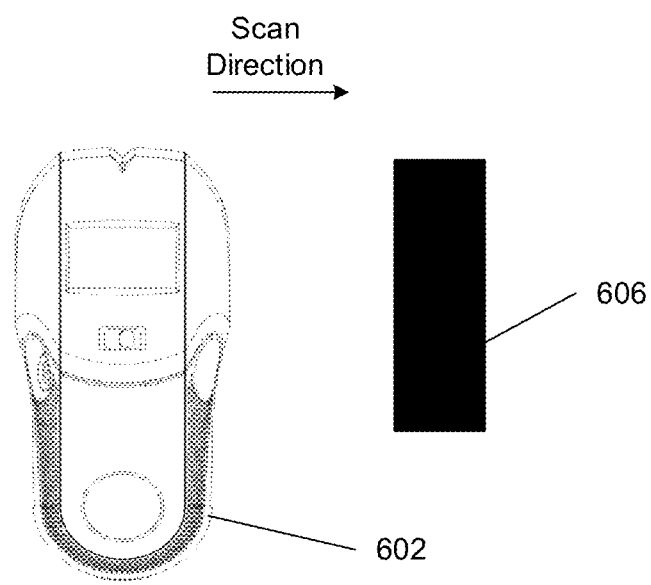
FIG. 6B illustrates a front view of the exemplary embodiment of FIG. 6A for differentiating the detected object according to aspects of the present invention.

FIG. 6B illustrates a front view of the exemplary embodiment of FIG. 6A for detecting the object according to aspects of the present invention. In the example of FIG. 6B, the opaque surface is not shown for simplicity. As shown in FIG. 6A and FIG. 6B, the scan direction may be from left to right. A person skilled in the art would understand that the scan direction may be adjusted based on the working environment, the preference of the user, and the specific application. In other words, the scan direction may be from left to right, right to left, up to down, down to up, or diagonally. In some applications, a user may perform multiple scans and/or from multiple directions to improve the accuracy of sensor data collected.

Figure 6C:
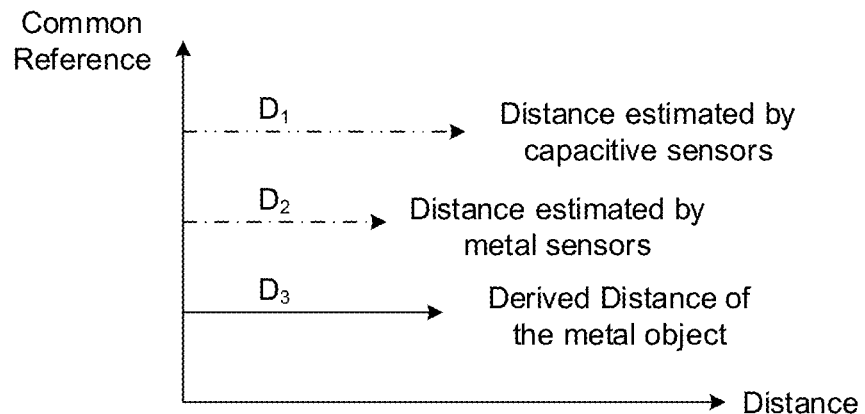
FIG. 6C illustrates an exemplary embodiment of determining a distance between the scanner and the object of FIG. 6B according to aspects of the present invention.

FIG. 6C illustrates an exemplary method of determining a distance between the scanner and the object of FIG. 6B according to aspects of the present invention. As shown in FIG. 6C, the vertical axis represents a common reference point or a common reference line from which a distance between scanner 602 and metal pipe 606 is estimated. The horizontal axis represents a distance from the common reference point or the common reference line. Scanner 602 may to configured to collect sensor data as described above in association with FIG. 2C and FIG. 2D. For example, based on the sensor data collected by one or more capacitive sensors of scanner 602, a first distance $D_1$, representing a distance between scanner 602 and metal pipe 606, may be estimated by the capacitive sensors.

In addition, based on the sensor data collected by one or more metal sensors of scanner 602, a second distance $D_2$, representing a distance between scanner 602 and metal pipe 606, may be estimated by the metal sensors. Note that although it is the same object (metal pipe 606) behind opaque surface 604, the capacitive sensors and the metal sensors may provide different estimations with respect to the distance between scanner 602 and metal pipe 606. In this exemplary embodiment, due to the presence of a large amount of metal, the metal sensors may provide an estimated distance (e.g. $D_2$) that is shorter than the actual distance between scanner 602 and metal pipe 606. On the other hand, the capacitive sensors may provide an estimated distance (e.g. $D_1$) that is closer to the actual distance between scanner 602 and the metal pipe 606.

From both of the sensor data collected by the capacitive sensors (not shown) and the sensor data collected by the metal sensors (not shown), scanner 602 may be configured to derive a distance $D_3$ for metal pipe 606 from the common reference. Thus, by using the sensor data collected by the capacitive sensors and the sensor data collected by the metal sensors, scanner 602 will obtain an improved estimation of the distance between scanner 602 and metal pipe 606 in this example. According to aspects of the present invention, both the sensor data collected by the capacitive sensors and the metal sensors may be collected in parallel in a one-pass scan, or multiple sets of sensor data may be collected by the capacitive sensors and the metal sensors in parallel with multiple passes, respectively.

Figure 7A:
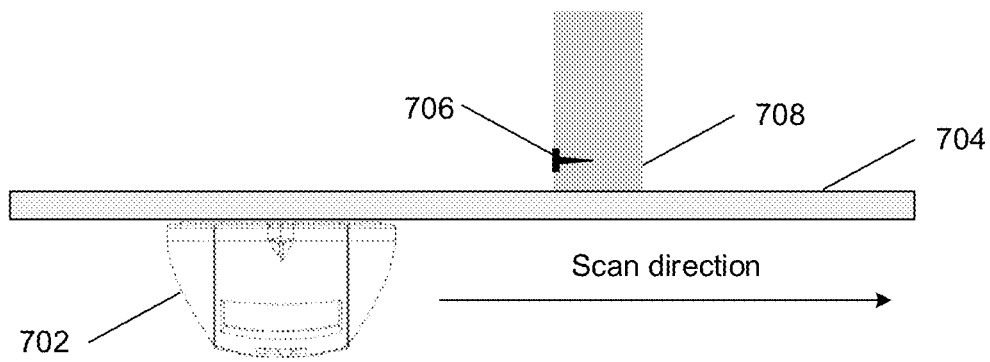
FIG. 7A illustrates a top view of an exemplary embodiment for detecting a metal object behind an opaque surface using sensor data from different sensors according to aspects of the present invention.

FIG. 7A illustrates a top view of an exemplary embodiment for differentiating object(s), here a metal screw 706 and stud 708, detected behind an opaque surface using sensor data from different sensors according to aspects of the present invention. As shown in FIG. 7A, the exemplary embodiment may include a scanner 702, an opaque surface 704, and one or more objects (labelled as 706 (metal screw) and 708 (stud)) behind opaque surface 704. In FIG. 7A, for example, object 706 may be a metal screw and for example, object 708 may be a wood stud.

Figure 7B:
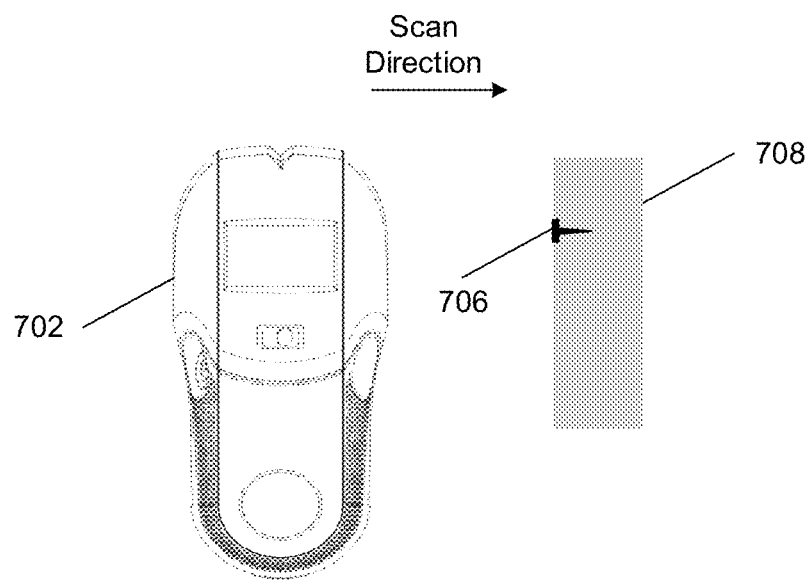
FIG. 7B illustrates a front view of the exemplary embodiment of FIG. 7A for detecting the metal object according to aspects of the present invention.

FIG. 7B illustrates a front view of the exemplary embodiment of FIG. 7A for detecting the metal object according to aspects of the present invention. As shown in FIG. 7A and FIG. 7B, the scan direction may be from left to right. A person skilled in the art would understand that the scan direction may be adjusted based on the working environment, the preference of the user, and the specific application. In other words, the scan direction may be from left to right, right to left, up to down, down to up, or diagonally. In some applications, a user may perform multiple scans and/or from multiple directions to improve the accuracy of sensor data collected.

Figure 7C:
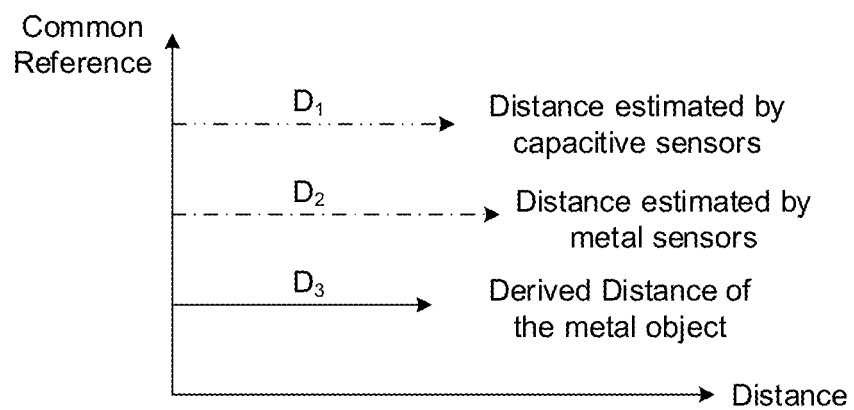
FIG. 7C illustrates an exemplary method of determining a distance between the scanner and the metal object of FIG. 7B according to aspects of the present invention.

FIG. 7C illustrates an exemplary method of determining a distance between the scanner and the metal object of FIG. 7B (screw 706) according to aspects of the present invention. As shown in FIG. 7C, the vertical axis represents a common reference point or a common reference line from which a distance between scanner 702 and metal screw 706 and stud 708 is estimated. The horizontal axis represents a distance from the common reference point or the common reference line. Scanner 702 may be configured to collect sensor data as described above in association with FIG. 2C and FIG. 2D. For example, based on the sensor data collected by one or more capacitive sensors of scanner 702, a first distance $D_1$, representing a distance between scanner 702 and metal screw 706 and stud 708 may be estimated by the capacitive sensors.

In addition, based on the sensor data collected by one or more metal sensors of scanner 702, a second distance $D_2$, representing a distance between scanner 702 and metal screw 706, may be estimated by the metal sensors. Note that the capacitive sensors and the metal sensors may provide different estimations with respect to the distance between scanner 702 and metal screw 706 based upon the relative size of the metal screw. In this exemplary embodiment, due to the presence of metal, the metal sensors may provide an estimated distance (e.g. $D_2$) that is different from the actual distance between scanner 702 and metal screw 706. On the other hand, the capacitive sensors may provide an estimated distance (e.g. $D_1$) that may be closer to the actual distance between scanner 702 and metal screw 706.

From both of the sensor data collected by the capacitive sensors and the sensor data collected by the metal sensors, scanner 702 may be configured to derive a distance $D_3$ for metal screw 706. Thus, by using the sensor data collected by the capacitive sensors and the sensor data collected by the metal sensors, scanner 702 may be able to obtain an improved estimation of the distance between scanner 702 and metal screw 706 in this example. According to aspects of the present invention, both the sensor data collected by the capacitive sensors and the metal sensors may be collected in parallel in a one-pass scan, or multiple sets of sensor data may be collected by the capacitive sensors and the metal sensors in parallel with multiple passes, respectively.

Figure 8:
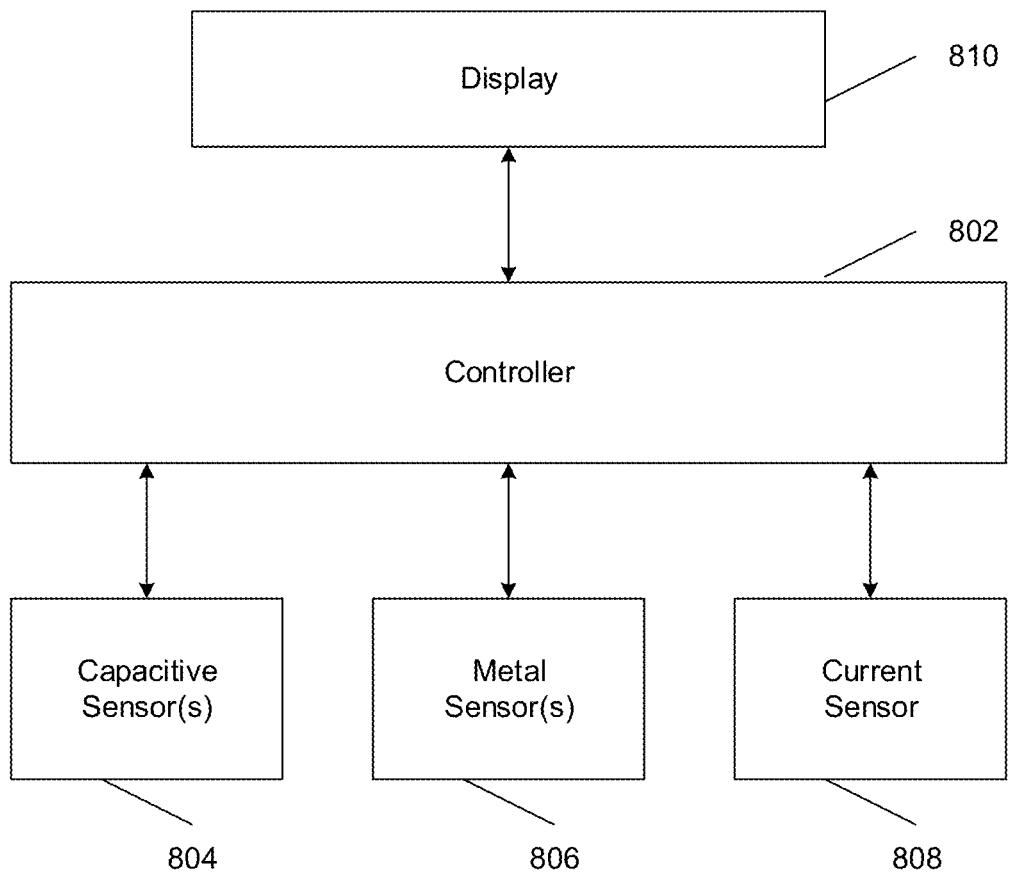
FIG. 8 illustrates a block diagram of an exemplary embodiment of a system for differentiating one or more objects detected behind an opaque surface using sensor data from different sensors according to aspects of the present invention.

FIG. 8 illustrates a block diagram of an exemplary embodiment of a system for differentiating one or more objects detected behind an opaque surface using sensor data from different sensors according to aspects of the present invention. In the exemplary system shown in FIG. 8, a controller 802 may be configured to process sensor data collected by sensors of the scanner, namely sensor data collected by capacitive sensors 804, metal sensor 806, and current sensor 808. The controller is further configured to determine information about the detected objects behind the opaque surface based on the sensor data collected by capacitive sensors 804, metal sensor 806, and/or current sensor 808 in parallel. The controller may include one or more processors. A display 810 is configured to provide information about the detected objects to a user.

According to aspects of the disclosure, the functional blocks described in the system of FIG. 8 may be implemented in an integrated device such as scanner 202 of FIG. 2A. In other implementations, the capacitive sensors 804, metal sensors 806, and current sensor 808 may reside in one device, while the controller 802 and the display 810 may reside in another device. For example, a scanner device may include the sensors, and the sensor data collected by the scanner device may be wirelessly communicated to a second device. The second device, for example a smartphone, a tablet, or a laptop, may include the controller 802 and the display 810. In yet other implementations, the controller 802, the capacitive sensors 804, metal sensors 806, and current sensor 808, may reside in one device, while the display 810 may reside in another device. For example, a scanner device may include the controller 802 and the sensors, and the sensor data collected by the scanner device may be wirelessly communicated to a second device. The second device, for example a monitor, may be configured to receive and display the sensor data.

According to aspects of the present disclosure, examples of capacitive sensors and methods of operating the same are described in U.S. Pat. No. 5,619,128, entitled "STUD SENSOR WITH OVER-STUD MISCALIBRATION VIA CIRCUIT WHICH STORES AN INITIAL CALIBRATION DENSITY, COMPARES THAT TO A CURRENT TEST DENSITY AND OUTPUTS RESULT VIA INDICATOR," which is incorporated herein in its entirety by reference. Examples of metal sensors and methods of operating the same are described in U.S. Pat. No. 7,812,722, entitled "DUAL ORIENTATION METAL SCANNER," which is incorporated herein in its entirety by reference. Examples of current sensors and methods of operating the same are described in U.S. Pat. No. 6,933,712, entitled "ELECTRICAL CIRCUIT TRACING AND IDENTIFYING APPARATUS AND METHOD," which is incorporated herein in its entirety by reference. In one exemplary embodiment, current sensors may be alternating current sensors. In another exemplary embodiment, current sensors may be able to detect the static magnetic field of or associated with direct current.

Figure 9A:
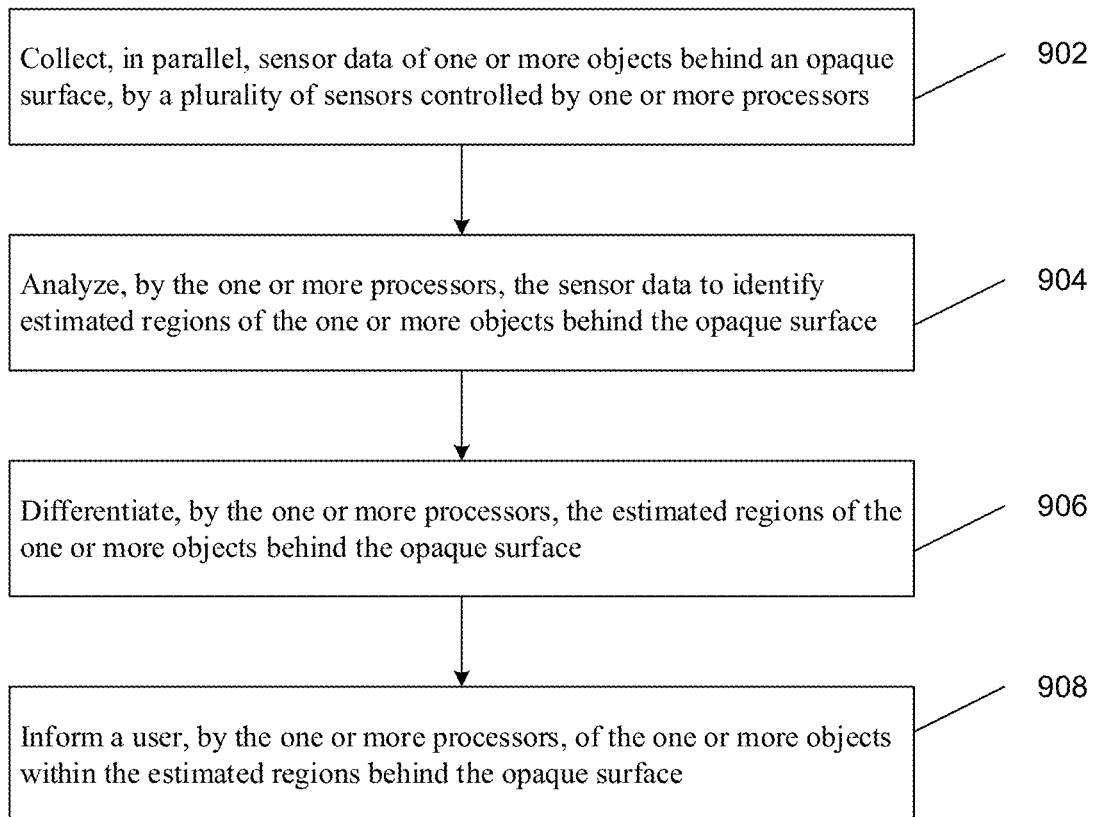
FIG. 9A illustrates a method of differentiating one or more objects detected behind an opaque surface using sensor data from different sensors according to aspects of the present invention.

FIG. 9A illustrates a method of differentiating one or more objects detected behind an opaque surface using sensor data from different sensors according to aspects of the present invention. As shown in FIG. 9A, in block 902, the method collects, in parallel, sensor data of the one or more objects behind an opaque surface, by a plurality of sensors controlled by one or more processors. In block 904, the method analyzes, by the one or more processors, the sensor data to identify estimated regions of the one or more objects behind the opaque surface. In block 906, the method differentiates, by the one or more processors, the estimated regions of the one or more objects behind the opaque surface. In block 908, the method informs a user, by the one or more processors, of the one or more objects within the estimated regions behind the opaque surface.

According to aspects of the present disclosure, the plurality of sensors may include at least a first set of sensors configured to detect a first type of material and a second set of sensors configured to detect a second type of material; and the estimated regions include a first estimated region of the first type of material and a second estimated region of the second type of material. The first set of sensors may include one or more capacitive sensors and the first type of material include wood studs; and the second set of sensors may include one or more metal sensors and the second type of material include metal objects. The plurality of sensors may further include a third set of sensors configured to detect a third type of material; where the third set of sensors includes one or more current sensors and the third type of material include electrical wires. According to aspects of the present disclosure, a set of sensors may include one or more sensors in the set.

The method of collecting sensor data includes mapping the sensor data of the one or more objects behind the opaque surface with respect to a common reference point. The method of differentiating the estimated regions of the one or more objects behind the opaque surface includes determining an overlap region between the first estimated region and the second estimated region.

Figure 9B:
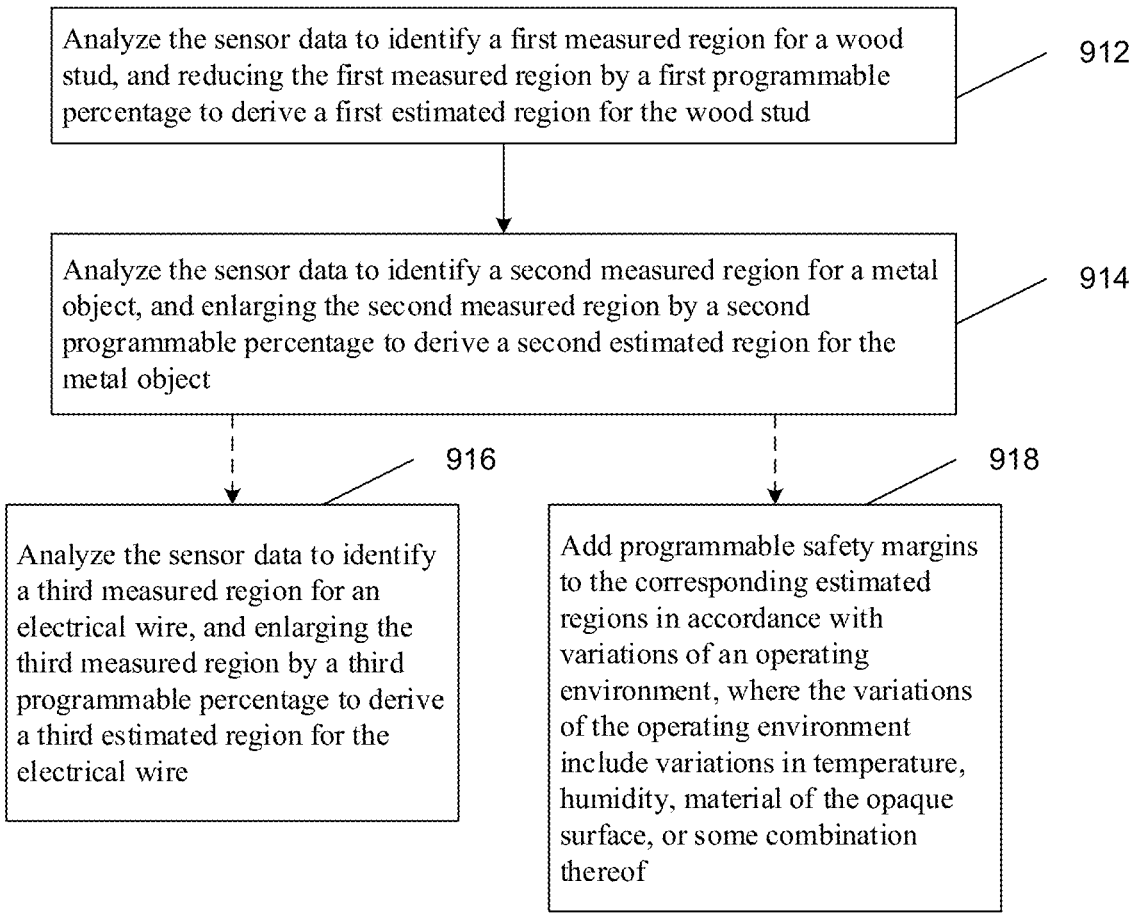
FIG. 9B illustrates a method of analyzing sensor data to identify estimated regions of the objects detected behind an opaque surface according to aspects of the present invention.

FIG. 9B illustrates a method of analyzing sensor data to identify estimated regions of the objects detected behind an opaque surface according to aspects of the present invention. In the exemplary embodiment of FIG. 9B, in block 912, the method analyzes the sensor data to identify a first measured region for a wood stud, and reducing the first measured region by a first programmable percentage to derive a first estimated region for the wood stud. In block 914, the method analyzes the sensor data to identify a second measured region for a metal object, and enlarging the second measured region by a second programmable percentage to derive a second estimated region for the metal object.

According to aspects of the present disclosure, the methods performed in block 912 and block 914 may additionally or optionally include the methods performed in block 916 and/or block 918. In block 916, the method analyzes the sensor data to identify a third measured region for an electrical wire, and enlarging the third measured region by a third programmable percentage to derive a third estimated region for the electrical wire. In block 918, the method adds programmable safety margins to the corresponding estimated regions in accordance with variations of an operating environment, where the variations of the operating environment include variations in temperature, humidity, material of the opaque surface, or some combination thereof.

Figure 9C:
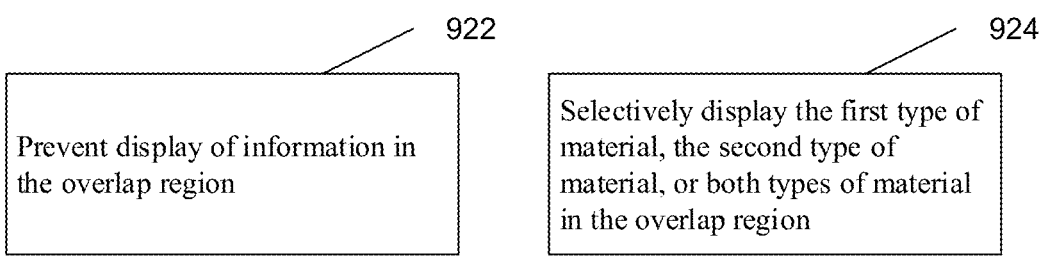
FIG. 9C illustrates a method of informing a user of the objects detected behind an opaque surface according to aspects of the present invention.

FIG. 9C illustrates a method of informing a user of the objects detected behind an opaque surface according to aspects of the present invention. In the example shown in FIG. 9C, the method described in either block 922 or block 924 may be performed. In block 922, the method prevents display of information in the overlap region. In block 924, the method selectively displays the first type of material, the second type of material, or both types of material in the overlap region.

It will be appreciated that the above descriptions for clarity have described embodiments of the invention with reference to different functional units and controllers. However, it will be apparent that any suitable distribution of functionality between different functional units or processors or controllers may be used without detracting from the invention. For example, functionality illustrated to be performed by separate processor(s) or controller(s) may be performed by the same processor(s) and/or controller(s) included with the unit. In another exemplary embodiment, functionality illustrated to be performed by the processor and/or controller or the display may be performed by an independent and/or remote receiving device, that may be able to display the information and/or provide a means accessible to the user. Hence, references to specific functional units are to be seen as references to suitable means for providing the described functionality rather than indicative of a strict logical or physical structure or organization.

The invention can be implemented in any suitable form, including hardware, software, firmware, or any combination of these. The invention may optionally be implemented partly as computer software running on one or more data processors and/or digital signal processors, along with the hardware components described above. The elements and components of an embodiment of the invention may be physically, functionally, and logically implemented in any suitable way. Indeed, the functionality may be implemented in a single unit, in a plurality of units, or as part of other functional units. As such, the invention may be implemented in a single unit or may be physically and functionally distributed between different units and processors/controllers.

One skilled in the relevant art will recognize that many possible modifications and combinations of the disclosed embodiments may be used, while still employing the same basic underlying mechanisms and methodologies. The foregoing description, for purposes of explanation, has been written with references to specific embodiments. However, the illustrative discussions above are not intended to be exhaustive or to limit the invention to the precise forms disclosed. Many modifications and variations are possible in view of the above teachings. The embodiments were chosen and described to explain the principles of the invention and their practical applications, and to enable others skilled in the art to best utilize the invention and various embodiments with various modifications as suited to the particular use contemplated.

What is claimed is:

1. A system for differentiating a plurality of objects detected behind an opaque surface, comprising:
   a plurality of sensors, controlled by one or more processors, configured to collect in parallel, sensor data of the plurality of objects behind an opaque surface;
   the one or more processors are configured to analyze the sensor data to identify estimated regions of the plurality of objects behind the opaque surface, wherein the plurality of sensors comprise at least a first set of sensors configured to detect a first type of material and a second set of sensors configured to detect a second type of material, and wherein the estimated regions include a first estimated region of the first type of material and a second estimated region of the second type of material;

the one or more processors are further configured to differentiate the estimated regions of the plurality of objects behind the opaque surface; and the one or more processors are further configured to inform a user, via a user interface, of the plurality of objects within the estimated regions behind the opaque surface.

2. The system of claim 1,
wherein the first set of sensors includes one or more capacitive sensors and the first type of material include wood studs; and
wherein the second set of sensors includes one or more metal sensors and the second type of material include metal objects.

3. The system of claim 1,
wherein the plurality of sensors further comprise a third set of sensors configured to detect a third type of material; wherein the third set of sensors includes one or more current sensors and the third type of material include electrical wires.

4. The system of claim 1, wherein the one or more processors are further configured to:
map the sensor data of the plurality of objects behind the opaque surface with respect to a common reference point.

5. The system of claim 1, wherein the one or more processors are further configured to:
analyze the sensor data to identify a first measured region for a wood stud, and reduce the first measured region by a first programmable percentage to derive a first estimated region for the wood stud; and
analyze the sensor data to identify a second measured region for a metal object, and enlarge the second measured region by a second programmable percentage to derive a second estimated region for the metal object.

6. The system of claim 5, wherein the one or more processor is further configured to:
analyze the sensor data to identify a third measured region for an electrical wire, and enlarge the third measured region by a third programmable percentage to derive a third estimated region for the electrical wire.

7. The system of claim 5, wherein the one or more processor is further configured to:
add programmable safety margins to the corresponding estimated regions in accordance with variations of an operating environment, wherein the variations of the operating environment include variations in temperature, humidity, material of the opaque surface, or some combination thereof.

8. The system of claim 1, wherein the one or more processors are further configured to:
determine an overlap region between the first estimated region and the second estimated region.

9. The system of claim 8, wherein the one or more processors are further configured to:
prevent display of information in the overlap region; or
selectively display the first type of material, the second type of material, or both types of material in the overlap region.

10. A method for differentiating a plurality of objects detected behind an opaque surface, comprising:
collecting, in parallel, sensor data of the plurality of objects behind an opaque surface, by a plurality of sensors controlled by one or more processors;
analyzing, by the one or more processors, the sensor data to identify estimated regions of the plurality of objects behind the opaque surface,
wherein the plurality of sensors comprise at least a first set of sensors configured to detect a first type of material and a second set of sensors configured to detect a second type of material, and wherein the estimated regions include a first estimated region of the first type of material and a second estimated region of the second type of material;
differentiating, by the one or more processors, the estimated regions of the plurality of objects behind the opaque surface; and
informing a user, by the one or more processors via a user interface, of the plurality of objects within the estimated regions behind the opaque surface.

11. The method of claim 10,
wherein the first set of sensors includes one or more capacitive sensors and the first type of material include wood studs; and
wherein the second set of sensors includes one or more metal sensors and the second type of material include metal objects.

12. The method of claim 10,
wherein the plurality of sensors further comprise a third set of sensors configured to detect a third type of material; wherein the third set of sensors includes one or more current sensors and the third type of material include electrical wires.

13. The method of claim 10, wherein collecting sensor data comprises:
mapping the sensor data of the plurality of objects behind the opaque surface with respect to a common reference point.

14. The method of claim 10, wherein analyzing the sensor data to identify estimated regions of the plurality of objects comprises:
analyzing the sensor data to identify a first measured region for a wood stud, and reducing the first measured region by a first programmable percentage to derive a first estimated region for the wood stud; and
analyzing the sensor data to identify a second measured region for a metal object, and enlarging the second measured region by a second programmable percentage to derive a second estimated region for the metal object.

15. The method of claim 14, further comprising:
analyzing the sensor data to identify a third measured region for an electrical wire, and enlarging the third measured region by a third programmable percentage to derive a third estimated region for the electrical wire.

16. The method of claim 14, wherein analyzing the sensor data to identify estimated regions of the plurality of objects further comprises:
adding programmable safety margins to the corresponding estimated regions in accordance with variations of an operating environment, wherein the variations of the operating environment include variations in temperature, humidity, material of the opaque surface, or some combination thereof.

17. The method of claim 10, wherein the differentiating comprises:
   determining an overlap region between the first estimated region and the second estimated region.

18. The method of claim 17, wherein informing the user comprises:
   preventing display of information in the overlap region; or
   selectively displaying the first type of material, the second type of material, or both types of material in the overlap region.

* * * * *